United States Patent [19]
Schavan et al.

[11] Patent Number: 6,059,785
[45] Date of Patent: May 9, 2000

[54] BONE FIXATION DEVICE

[75] Inventors: Robert Schavan, Davos Dorf; Robert Frigg, Davos Platz, both of Switzerland

[73] Assignee: Synthes (U.S.A.), Paoli, Pa.

[21] Appl. No.: 08/340,905

[22] Filed: Nov. 15, 1994

[30] Foreign Application Priority Data

Dec. 7, 1993 [CH] Switzerland .................. 3643/93

[51] Int. Cl.$^7$ ........................................ A61B 17/58
[52] U.S. Cl. ........................ 606/73; 606/72; 606/61
[58] Field of Search ............................. 606/54, 60, 61, 606/69, 70, 71, 72, 73, 80

[56] References Cited

U.S. PATENT DOCUMENTS

| | | | |
|---|---|---|---|
| 2,494,229 | 1/1950 | Collison | 606/73 |
| 4,360,012 | 11/1982 | McHarrie et al. | 606/54 |
| 4,463,753 | 8/1984 | Gustilo | 606/73 |
| 4,537,185 | 8/1985 | Stednitz | 606/73 |
| 4,714,076 | 12/1987 | Comte et al. | |
| 4,978,350 | 12/1990 | Wagenknecht | 606/73 |
| 5,242,447 | 9/1993 | Borzone | 606/73 |

FOREIGN PATENT DOCUMENTS 0153546  1/1988  European Pat. Off. .

*Primary Examiner*—Michael Buiz
*Assistant Examiner*—Daphna Shai
*Attorney, Agent, or Firm*—Fish & Richardson P.C.

[57] ABSTRACT

A bone fixation device has a shaft threaded at the head end and shaped as a drill toward the tip.

9 Claims, 2 Drawing Sheets

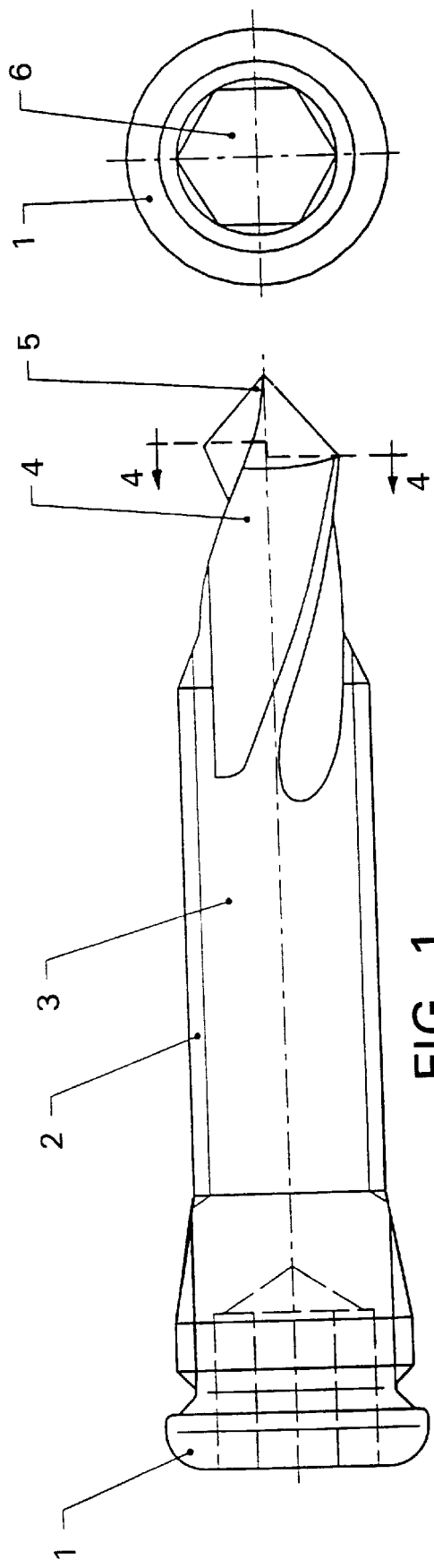

BONE FIXATION DEVICE

FIELD OF THE INVENTION

The invention relates to a bone fixation device, specifically a bone screw.

BACKGROUND OF THE INVENTION

Bone screws and wires find wide-ranging applications in osteosynthesis. In osteosynthesis bone screws are used for fixation of bone fragments as well as attachment of longitudinal support rods. Wires are used to fix bone fragments.

Conventional bone screws, particularly the so-called Schanz screws, are used in osteosynthesis for a multiplicity of purposes in positioning and fixing bone fragments. An example of this are components of an osteosynthetic external fixation device (such as that of EP-B1 0 153 546), which in essence consists of one or more connected longitudinal support rods, that can be disconnected from each other, along with the attached clamps or clasps for receiving the Schanz screws. Such an application requires that prior to the placement of the Schanz screws an appropriate hole be drilled into the bone, into which the Schanz screw can then be screwed. This procedure is complex and time-consuming.

The thread pitch of a bone screw is critical, for it determines the cutting rate (i.e., the advance) of the screw. In other words, for each turn the screw is forced to go forward by the length of the screw pitch. If a screw pitch of about 1.75 mm, typical for bone screws, is selected, then the tip of the tap used to thread the hole will advance an increment of 1.75 mm for each turn. Assuming a drilling machine with a normal rotational speed of about 600 to 800 r.p.m., typically employed in bone surgery is used to drive the tap, this results in an advance of more than a meter per minute. The extraordinarily intense pressure on the bone caused by this advance to the tap tip can result in spontaneous tears or fractures in the bone. The principal disadvantage of having too rapid an advance is evident primarily when the tip has passed through the proximal corticalis and the medullary space and encounters the inner side of the counter-corticalis. There the tip has no chance of centering itself and producing a so-called channel. Instead of the bone being drilled through, it is thrust away by the tip. This leads inevitably to a splitting of the counter-corticalis. If the screw is inserted near the fracture, the applied pressure is dispersed through longitudinal fissures of the counter-corticalis.

Efforts to reduce the axial pressure by reducing the drill r.p.m. are not possible, since the advance is preset by the thread pitch of the screw.

The manipulation procedures for the insertion of bone screws are also extended. The screw hole must first be bored out with an initial instrument, and then a second instrument must be used to cut the thread. Finally, in a third procedure, the bone screw is screwed in. It is also not uncommon to have a typical bone screw tightened to the limit of its retention force, in order to fix longitudinal support rods or bone plates on the bone. This is necessary since there is no stable connection between bone screws and the support rods or plates. Owing to the often very high initial stress, up to the retention force limit, screws can tear loose from the bone.

In addition, during the procedure described above, errors can accumulate, resulting in a poor fixation.

Wires can be inserted into bone without large-scale preliminary work, but they damage the bone owing to the associated high temperatures which arise from friction between bone and wire. In addition, the axial stability of bone fragments fixed with wires is not very great, so that the result may be a loss of positioning.

SUMMARY OF THE INVENTION

In accordance with the invention, these difficulties are met by a bone fixation device having a tip shaped like a drill. Specifically, the invention comprises a bone fixation device comprising a shaft having a head and a tip, the part of said shaft adjacent said tip being shaped as a spiral drill and at least a part of the shaft adjacent the head being threaded.

Stated another way, the first part (i.e. the part near the tip) of a device according to the invention is shaped as a self-cutting, self-drilling, double lipped spiral drill. Its exterior is at most the diameter of the root of the threaded portion. The front part is advantageously 3–18 mm, preferably 4–12 mm long.

BRIEF DESCRIPTION OF THE DRAWINGS

The invention will be further described with reference to the accompanying drawing in which:

FIG. 1 is a schematic representation of a bone-fixation device according to the invention.

FIG. 2 is an axial view of the bone fixation device according to FIG. 1.

FIG. 3 is a longitudinal section detail through the winding of the bone fixation device according to FIG. 1.

FIG. 4 is a cross section along the line 4—4 of FIG. 1.

DETAILED DESCRIPTION OF THE DRAWINGS

Figure 5:
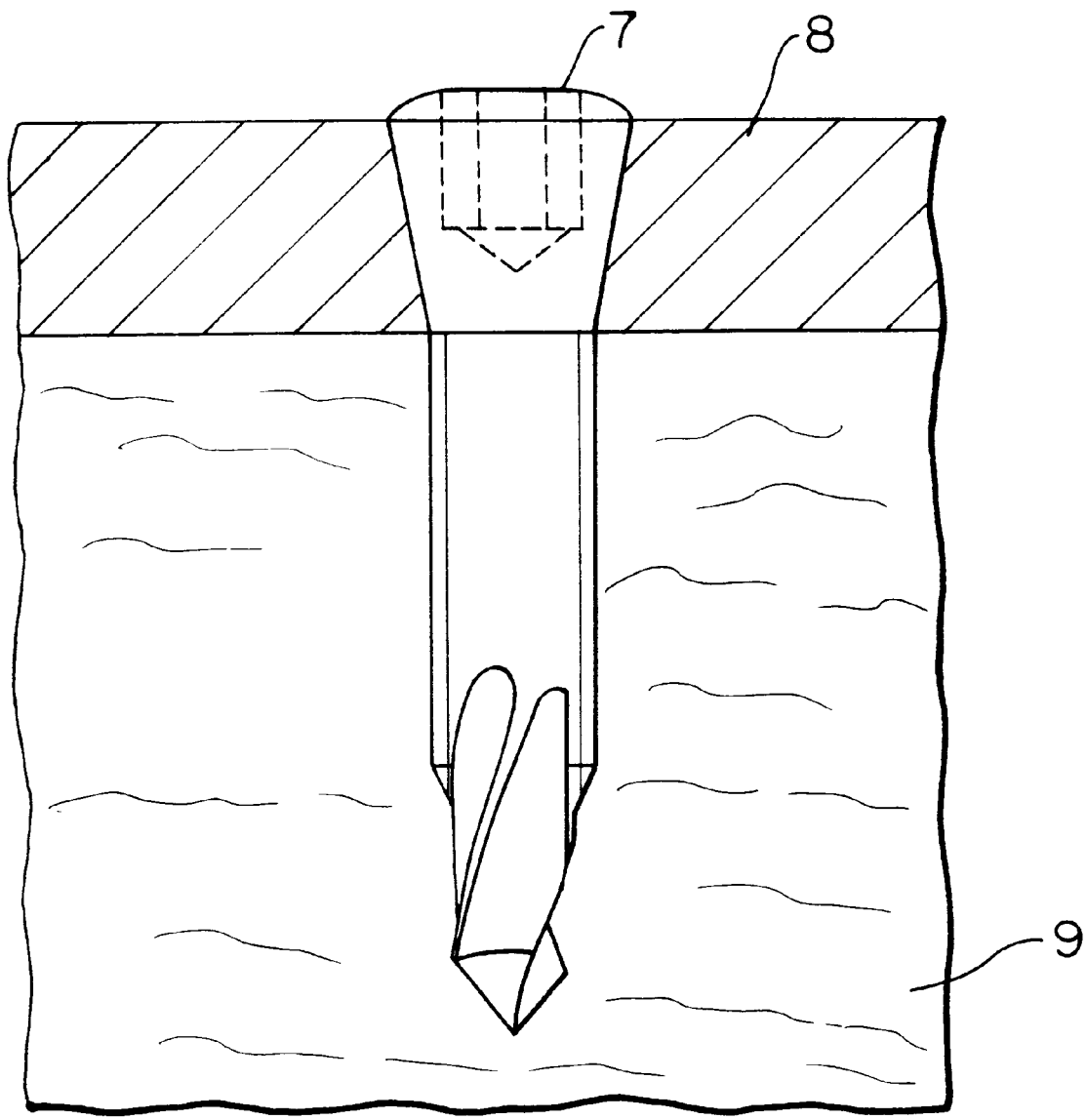
FIG. 5 is a side elevational view, partly in vertical section, showing a screw and plate according to the invention attached to a bone.

The bone fixation device shown in FIGS. 1–4 essentially consists of a head part 1, a shaft 3 provided with a thread 2, and a front part 4 with a tip 5.

The front part 4 is shaped as a self-cutting, self-drilling, double-lipped spiral drill, whose exterior diameter is smaller than the core diameter of thread 2. The drill shape extends the full length of front part 4. Front part 4 most preferably has a length of 7–9 mm, depending on the total length of the device.

The head end 1, as shown in FIG. 2, is provided with a central indentation 6 in the form of a hexagonal socket; this serves for admission of an instrument for screwing the device in a bone. The thread 2 may be a self-tapping thread.

The dimensions of the spiral drill are preferably as follows:

| | |
|---|---|
| Point angle | 60–120°, preferably 80–90° |
| Rake or helix angle | 10–40°, preferably 20–30° |
| Margin | 0.2–1.0 mm, preferably 0.3–0.6 mm |
| Screw height | 0.3–1.5 mm, preferably 0.6–0.8 mm |
| Drill core | 0.1–0.6, preferably 0.3–0.5 times the outside diameter |

The bone fixation device can have a multiplicity of applications. For example, it can be used for fixation of bone plates. This is shown in FIG. 5 where a screw 7 according to the invention is shown attaching a bone plate 8 to a bone 9. It can also be used as an attachment component for external fixation systems comprising support rods and clamps used in osteosynthesis.

In use the device according to the invention is applied as one would apply a normal self-tapping screw, driving the device in manually with a suitable screwdriver.

What is claimed is:

1. A bone plate assembly comprising a bone plate having screw holes and a bone fixation device in a screw hole of said plate, said bone fixation device having a shaft with a head and a tip, a part of the shaft adjacent the tip being shaped as a drill and another part of the shaft having a thread, wherein the part shaped as a drill is self-drilling and self-cutting.

2. The bone plate assembly according to claim 1 wherein the thread has a minor diameter and the part shaped as a drill has a maximum exterior diameter which is at most equal to the minor diameter of the thread.

3. The bone plate assembly according to claim 2 wherein the part shaped as a drill is from 3 to 18 mm long.

4. The bone plate assembly according to claim 3 wherein the part shaped as a drill is from 4 to 12 mm long.

5. The bone plate assembly according to claim 2 wherein the thread extends out into the part of the shaft.

6. The bone plate assembly according to claim 2 and comprising a central indentation in said head for admitting an instrument for screwing the device into a bone.

7. The bone plate assembly of claim 6 wherein the indentation is a hexagonal socket.

8. A bone plate assembly comprising a bone plate having screw holes and a bone fixation device in a screw hole of said plate, said bone fixation device having a shaft with a head and a tip, a part of the shaft adjacent the tip being shaped as a drill and another part of the shaft having a thread, wherein the part shaped as a drill is shaped as a spiral drill.

9. A bone plate assembly comprising a bone plate having screw holes and a bone fixation device in a screw hole of said plate, said bone fixation device having a shaft with a head and a tip, a part of the shaft adjacent the tip being shaped as a drill and another part of the shaft having a thread, wherein the part of the shaft adjacent to the tip is shaped as a double-lipped drill.

* * * * *